US008532752B2

(12) United States Patent
Kim et al.

(10) Patent No.: US 8,532,752 B2
(45) Date of Patent: Sep. 10, 2013

(54) BIOSIGNAL AMPLIFYING DEVICE

(75) Inventors: Jong Pal Kim, Seoul (KR); Kun Soo Shin, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1416 days.

(21) Appl. No.: 12/004,422

(22) Filed: Dec. 21, 2007

(65) Prior Publication Data

US 2008/0150631 A1    Jun. 26, 2008

(30) Foreign Application Priority Data

Dec. 26, 2006 (KR) .......................... 10-2006-0133569

(51) Int. Cl.
*A61B 5/04* (2006.01)
*H03F 3/68* (2006.01)

(52) U.S. Cl.
USPC .......................................... 600/509; 330/103

(58) Field of Classification Search
USPC .......................................... 600/509; 330/103
See application file for complete search history.

(56) References Cited

U.S. PATENT DOCUMENTS

| | | | | |
|---|---|---|---|---|
| 4,313,442 A | * | 2/1982 | Knudson et al. | 607/17 |
| 4,697,152 A | * | 9/1987 | Westwick | 330/9 |
| 4,926,135 A | * | 5/1990 | Voorman | 330/107 |
| 5,105,163 A | * | 4/1992 | Voorman | 330/107 |
| 7,106,131 B2 | * | 9/2006 | Lee et al. | 330/69 |

FOREIGN PATENT DOCUMENTS

| | | |
|---|---|---|
| JP | 60-103808 | 6/1985 |
| JP | 5-220121 | 8/1993 |
| JP | 6-315470 | 11/1994 |
| JP | 11-332839 | 12/1999 |
| KR | 1020050106869 | 11/2005 |

OTHER PUBLICATIONS

Korean Office Action issued on Aug. 25, 2008 in corresponding Korean Patent Application No. 10-2006-0133569.

* cited by examiner

*Primary Examiner* — Tammie K Heller
(74) *Attorney, Agent, or Firm* — Staas & Halsey LLP

(57) ABSTRACT

A biosignal amplifying device includes: an operational amplifier (op-amp); a capacitor load including a first capacitor connected with a first input terminal of the op-amp, and in which a first voltage is inputted from a first electrode, and a second capacitor which is connected with a second input terminal of the op-amp, and in which a second voltage is inputted from a second electrode; a feedback capacitor load including a first feedback capacitor connected with the first input terminal and an output terminal, and a second feedback capacitor connected with the second input terminal; and a feedback resistor load including a first feedback resistor connected with the first input terminal and the output terminal, and a second feedback resistor connected with the second input terminal.

12 Claims, 1 Drawing Sheet

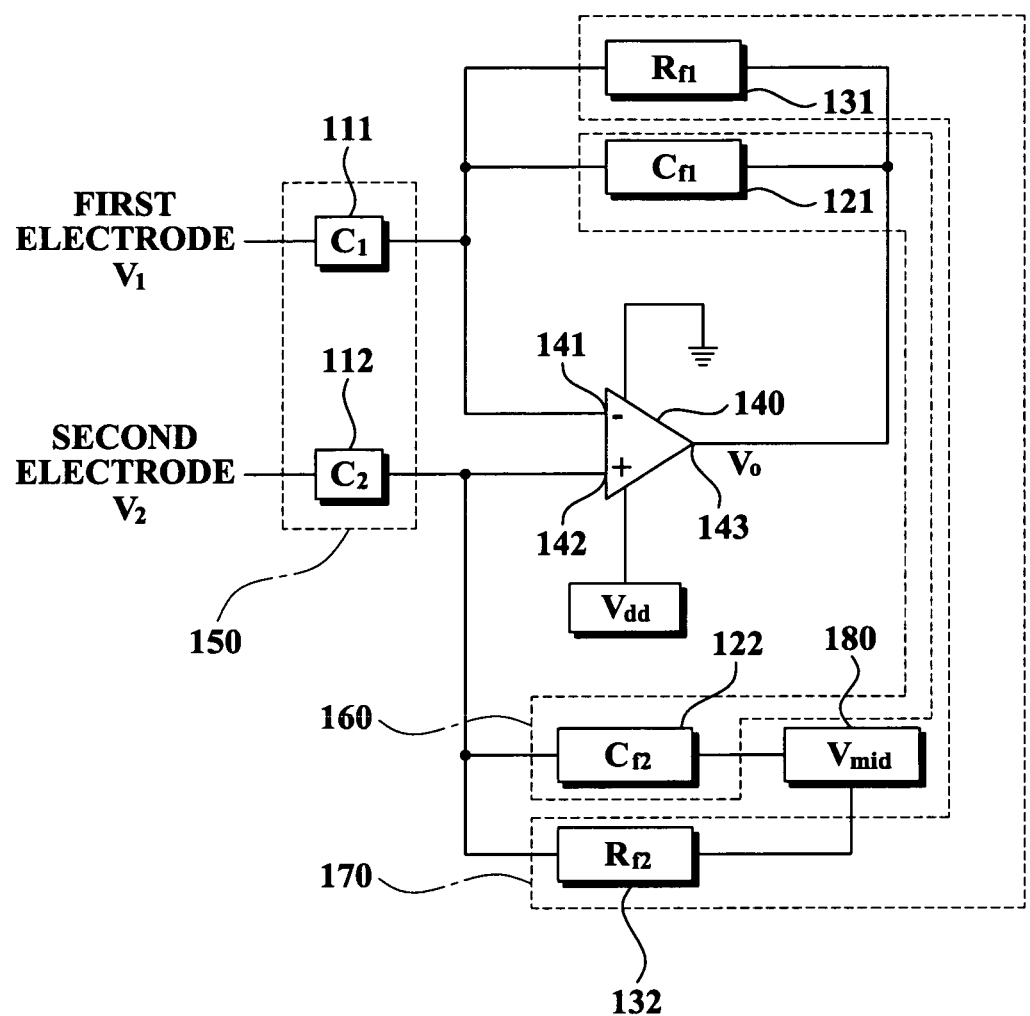

BIOSIGNAL AMPLIFYING DEVICE

CROSS-REFERENCE TO RELATED APPLICATION

This application claims the benefit of Korean Patent Application No. 10-2006-0133569, filed on Dec. 26, 2006, in the Korean Intellectual Property Office, the disclosure of which is incorporated herein by reference.

BACKGROUND

1. Field

One or more embodiments relate to a biosignal amplifying circuit, and more particularly, to a biosignal amplifying circuit which can amplify and filter a biosignal measured from a user via an electrode in a biosignal measurement apparatus measuring the biosignal from the user via the predetermined electrode.

2. Description of the Related Art

As used in the embodiment, the term "Ubiquitous" means an information communication environment where a user can be free to access networks at any place without being conscious of the surrounding networks or computers. If ubiquitous is commercialized, anyone can readily use information technology not only at home or in a car, but also even on a mountaintop. Also, the commercialization of Ubiquitous may expand the information technology industry or the scope corresponding thereto by increasing the number of computer users who are connected to networks. Because of its advantage that users can access networks without restriction to time and place, not to mention its portability and convenience, countries worldwide are expanding development and competing in Ubiquitous-related technology now.

Ubiquitous-related technology may be applied to any field in human life. Particularly, a Ubiquitous-Health Care (hereinafter, U-HealthCare) has recently been in the spotlight as a remarkable technology field owing to a recent health craze and "well-being" phenomenon among people. U-Health Care refers to a ubiquitous technology in which chips or sensors associated with a medical service are installed at various living spaces of the human being so that all the people can be naturally provided with medical services anytime and anywhere. According to such a U-Health Care, health care in hospitals including various kinds of health diagnoses, disease management, emergency management, consultation with a doctor, etc., can be naturally implemented in each person's daily life without having to actually visit the hospital.

For example, a diabetic may wear a belt having a blood-sugar management program for blood-sugar management. A blood-sugar sensor attached to the belt may check the blood-sugar of the diabetic upon a specified occasion, and calculate the amount of required insulin corresponding thereto. When the blood-sugar of the diabetic becomes drastically low or high, the belt may provide the blood-sugar information to his/her attending physician via a wireless network, and the attending physician who has received the blood-sugar information may write out an optimal prescription or take the optimal action for the medical emergency.

As an example of U-HealthCare, a portable electrocardiogram measurement device is currently commercialized, and is used for users suffering from cardiac diseases. A portable electrocardiogram measurement device, which may be portable, may constantly measure an electrocardiogram, and cope with sudden cardiac diseases considering a characteristic of cardiac diseases that may be suffered from anytime and anywhere, may correspond to a device showing a significant advantage of U-HealthCare.

An electrocardiogram measurement device corresponds to an apparatus for obtaining an electrocardiogram waveform for sensing a weak electrocardiogram generated in a body, and determining whether a cardiac disease exists. Accordingly, elements such as a structure of an electrode, a shape, a material, and the like for sensing a weak electrocardiogram signal, which is generated in a body, have a significant effect on performance and utility of an entire measurement system, in a portable electrocardiogram measurement device.

An electrocardiogram is measured via a plurality of electrodes considering a characteristic of the electrocardiogram. Specifically, an electrocardiogram of a user may be measured via at least two electrodes. According to a related art, after an electrocardiogram signal measured from a user via the at least two electrodes is inputted through a buffer connected with each electrode, the electrocardiogram signal is amplified by an amplifier, and is filtered using a high pass filter (HPF).

Next, the signal, amplified and filtered using the HPF, is processed via a predetermined signal processing module, and the signal processing module may measure and interpret the electrocardiogram of the user. Accordingly, a process of amplifying an electrocardiogram signal measured via an electrode, and filtering the electrocardiogram signal using an HPF is a flow generally required to perform when the electrocardiogram signal is measured. The above flow is generally applicable to all biosignal measurements besides an electrocardiogram signal.

A biosignal measurement apparatus according to a related art includes at least two buffers, an amplifier, and an HPF as a configuration of a biosignal amplifying module for amplifying a biosignal measured via an electrode and filtering the biosignal using an HPF. Specifically, when each biosignal is inputted through at least two buffers connected with at least two electrodes, the biosignal is amplified by the amplifier. Next, a predetermined process is performed based on a signal filtered using the HPF.

The configuration is complicated since it is required that a biosignal measurement apparatus according to a related art should include a plurality of multistage operational amplifiers in order to respectively include the at least two buffers, the amplifier, and the HPF as a configuration of a biosignal amplifying circuit. Therefore, the biosignal measurement apparatus according to the related art has a drawback of being unfavorable for miniaturization.

Also, since an amplifier according to a related art includes a predetermined active element chip, a configuration of a biosignal amplifying circuit becomes more complex and larger. Accordingly, there is a problem that an amplifier according to a related art is unfavorable for a portable biosignal measurement apparatus enabling miniaturization and slimming.

Therefore, a biosignal amplifying device, which can simplify a biosignal amplifying circuit amplifying and filtering a biosignal measured from a user via an electrode in a biosignal measurement apparatus more significantly, and enable miniaturization, slimming, and minimization of production costs, is required.

SUMMARY

Additional aspects and/or advantages will be set forth in part in the description which follows and, in part, will be apparent from the description, or may be learned by practice of the invention.

An aspect of the embodiment provides a biosignal amplifying device which can include a biosignal amplifying circuit having one operational amplifier (op-amp) and a high pass filter (HPF) with one stage, thereby enabling miniaturization and slimming when the biosignal amplifying circuit is realized in a printed circuit board (PCB), or an application specific integrated circuit (ASIC) using a commercialized integrated circuit (IC).

According to an aspect of the embodiment, there is provided a biosignal amplifying device including: an op-amp; a capacitor load including a first capacitor connected with a first input terminal of the op-amp, and in which a first voltage is inputted from a first electrode, and a second capacitor which is connected with a second input terminal of the op-amp, and in which a second voltage is inputted from a second electrode; a feedback capacitor load including a first feedback capacitor connected with the first input terminal and an output terminal, and a second feedback capacitor connected with the second input terminal; and a feedback resistor load including a first feedback resistor connected with the first input terminal and the output terminal, and a second feedback resistor connected with the second input terminal.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 1 is a circuit diagram illustrating a configuration of a biosignal amplifying device according to an exemplary embodiment.

DETAILED DESCRIPTION OF THE EMBODIMENTS

Reference will now be made in detail to exemplary embodiments of the present invention, examples of which are illustrated in the accompanying drawings, wherein like reference numerals refer to the like elements throughout. The exemplary embodiments are described below in order to explain the embodiment by referring to the figures.

A biosignal amplifying device according to an exemplary embodiment may be realized in amplifying and filtering various biosignals measured from a user via a predetermined electrode. For example, the biosignal amplifying circuit may amplify and filter an electrocardiogram (ECG) signal of a user, a photoplethymogram (PPG) signal, a galvanic skin response (GSR) signal, an electroencephalogram (EEG) signal, an electroculogram (EOG) signal, or an electromyogram (EMG) signal, among other biosignals.

For convenience of description, a case that a biosignal measurement apparatus measures an ECG signal of a user via two electrodes, and a biosignal amplifying circuit amplifies the ECG signal, and filters the ECG signal using a high pass filter (HPF) is described as an example of an aspect of the embodiment.

Hereinafter, an aspect of an exemplary embodiment is described in detail with reference to an appended drawing.

FIG. 1 is a circuit diagram illustrating a configuration of a biosignal amplifying device according to an exemplary embodiment.

The biosignal amplifying device according to the present exemplary embodiment may include an operational amplifier (op-amp) 140, a capacitor load 150, a feedback capacitor load 160, and a feedback resistor load 170.

The capacitor load 150 includes a first capacitor 111 and a second capacitor 112. The feedback capacitor load 160 includes a first feedback capacitor 121 and a second feedback capacitor 122. Also, the feedback resistor load 170 includes a first feedback resistor 131 and a second feedback resistor 132.

The biosignal amplifying device according to the exemplary embodiment may be realized in a portion of a configuration of a predetermined biosignal measurement apparatus. The biosignal measurement apparatus may electrically measure a biosignal via a first electrode and a second electrode contacting with a bio-tissue of a user. The first electrode and the second electrode may be realized in a dry-type electrode or a wet-type electrode. Also, the first electrode and the second electrode may be realized including various electrode types widely used in the art for measuring a biosignal of a user.

The first capacitor 111 is connected with a first input terminal of the op-amp 140, and a first electrode. The first input terminal indicates an inverting input terminal 141 of the op-amp 140, or a non-inverting input terminal 142. Specifically, the first capacitor 111 may be connected with the inverting input terminal 141 of the op-amp 140, or the non-inverting input terminal 142. The first capacitor 111 is connected with the inverting input terminal 141 is described as an example in the embodiment.

A first voltage is inputted in the first capacitor 111 from a first electrode. The first voltage may be realized in a voltage of a biosignal which the first electrode measures from a user. Accordingly, the first voltage inputted in the first capacitor 111 may be inputted in the inverting input terminal 141 of the op-amp 140.

The second capacitor 112 is connected with a second input terminal of the op-amp 140, and a second electrode. The second input terminal indicates the inverting input terminal 141 of the op-amp 140, or the non-inverting input terminal 142. Specifically, the second capacitor 112 may be connected with the inverting input terminal 141 of the op-amp 140, or the non-inverting input terminal 142. The second capacitor 112 is connected with the non-inverting input terminal 142 is described as an example in the embodiment.

A second voltage is inputted in the second capacitor 112 from a second electrode. The second voltage may be realized in a voltage of a biosignal which the second electrode measures from a user. Accordingly, the second voltage inputted in the second capacitor 112 may be inputted in the non-inverting input terminal 142 of the op-amp 140.

The first feedback capacitor 121 is connected with the first input terminal of the op-amp 140 and an output terminal 143. The first input terminal indicates the inverting input terminal 141 of the op-amp 140, or the non-inverting input terminal 142. Specifically, the first feedback capacitor 121 may be connected with the inverting input terminal 141 of the op-amp 140, or the non-inverting input terminal 142. The first feedback capacitor 121 is connected with the inverting input terminal 141 is described as an example in the embodiment.

The second feedback capacitor 122 is connected with the second input terminal of the op-amp 140. The second input terminal indicates the inverting input terminal 141 of the op-amp 140, or the non-inverting input terminal 142. Specifically, the second feedback capacitor 122 may be connected with the inverting input terminal 141 of the op-amp 140, or the non-inverting input terminal 142. The second feedback capacitor 122 is connected with the non-inverting input terminal 142 is described as an example of the embodiment.

The first feedback resistor 131 is connected with the first input terminal of the op-amp 140 and the output terminal 143. The first input terminal indicates the inverting input terminal 141 of the op-amp 140, or the non-inverting input terminal 142. Specifically, the first feedback resistor 131 may be connected with the inverting input terminal 141 of the op-amp 140, or the non-inverting input terminal 142. The first feedback resistor 131 is connected with the inverting input terminal 141 is described as an example of the embodiment.

The second feedback resistor 132 is connected with the second input terminal of the op-amp 140. The second input terminal indicates the inverting input terminal 141 of the op-amp 140, or the non-inverting input terminal 142. Specifically, the second feedback resistor 132 may be connected with the inverting input terminal 141 of the op-amp 140, or the non-inverting input terminal 142. The second feedback resistor 132 is connected with the non-inverting input terminal 142 is described as an example of the embodiment.

As illustrated in FIG. 1, the first feedback capacitor 121 and the first feedback resistor 131 are connected with the inverting input terminal 141 of the op-amp 140, the first capacitor 111, and the output terminal 143 of the op-amp 140. Also, the first feedback capacitor 121 and the first feedback resistor 131 are connected in parallel.

The second feedback capacitor 122 and the second feedback resistor 132 are connected with the non-inverting input terminal 142 of the op-amp 140, and the second capacitor 112. Also, the second feedback capacitor 122 and the second feedback resistor 132 are connected in parallel. Also, a direct current (DC) offset voltage ($V_{mid}$) 180 may be supplied to the second feedback capacitor 122 and the second feedback resistor 132.

Similar to the description above, the biosignal amplifying circuit according to an exemplary embodiment may be realized by being respectively connected with the first capacitor 111, the second capacitor 112, the first feedback capacitor 121, the second feedback capacitor 122, the first feedback resistor 131, and the second feedback resistor 132, centering the one op-amp 140. The biosignal amplifying circuit according to an exemplary embodiment may amplify a biosignal inputted from the first electrode and the second electrode, and filter the biosignal using a low pass filter (LPF) and an HPF according to a configuration of the circuit, as constructed above.

Hereinafter, an example of an operation that the biosignal amplifying circuit illustrated in FIG. 1 amplifies a biosignal and filters the biosignal using an LPF and an HPF is described in detail. For convenience of description, a case in which a capacitance (C) of the first capacitor 111 and a capacitance (C) of the second capacitor 112 are identical, and a capacitance ($C_f$) of the first feedback capacitor 121 and a capacitance ($C_f$) of the second feedback capacitor 122 are identical, and a resistance ($R_f$) of the first feedback resistor 131 and a resistance ($R_f$) of the second feedback resistor 132 are identical, is described.

The first electrode and the second electrode respectively have resistance components. Accordingly, a first LPF may be formed by the first electrode and the first capacitor 111. Also, a second LPF may be formed by the second electrode and the second capacitor 112.

For example, when a resistance value of the first electrode is $R_1$, a cut-off frequency of the first LPF may be established as $1/(2\pi*R_1*C)$. Also, when a resistance value of the second electrode is $R_2$, a cut-off frequency of the second LPF may be established as $1/(2\pi*R_2*C)$.

As described above, a low pass filtering may be performed using the first electrode and the first capacitor 111, and another low pass filtering may be performed using the second electrode and the second capacitor 112. Specifically, the low pass filtering to the desired cut-off frequency may be performed by respectively controlling the capacitance of the first capacitor 111 and the capacitance of the second capacitor 112.

A gain of the op-amp 140 may be determined according to any one capacitance from among the capacitor load, and any one capacitance from among the feedback capacitor load.

Specifically, the gain may be determined according to any one capacitance from among the first capacitor 111 and the second capacitor 112, and any one capacitance from among the first feedback capacitor 121 and the second feedback capacitor 122.

In this instance, the gain of the op-amp 140 may correspond to $C/C_f$ when the capacitance (C) of the first capacitor 111 and the capacitance (C) of the second capacitor 112 are identical, and the capacitance ($C_f$) of the first feedback capacitor 121 and the capacitance ($C_f$) of the second feedback capacitor 122 are identical, and the resistance ($R_f$) of the first feedback resistor 131 and the resistance ($R_f$) of the second feedback resistor 132 are identical, similar to the description above.

Accordingly, the biosignal amplifying device according to an exemplary embodiment may amplify the biosignal up to the gain $C/C_f$.

Also, the cut-off frequency for the high pass filtering of the op-amp 140 may be determined according to any one resistance from among the feedback resistor load, and any one capacitance from among the feedback capacitor load.

Specifically, the cut-off frequency for the high pass filtering may be determined according to any one resistance from among the first feedback resistor 131 and the second feedback resistor 132, and any one capacitance from among the first feedback capacitor 121 and the second feedback capacitor 122.

In this instance, the cut-off frequency for the high pass filtering may correspond to $1/(2\pi*R_f*C_f)$ when the capacitance (C) of the first capacitor 111 and the capacitance (C) of the second capacitor 112 are identical, and the capacitance ($C_f$) of the first feedback capacitor 121 and the capacitance ($C_f$) of the second feedback capacitor 122 are identical, and the resistance ($R_f$) of the first feedback resistor 131 and the resistance ($R_f$) of the second feedback resistor 132 are identical, similar to the description above.

Accordingly, the biosignal amplifying device according to the exemplary embodiment may filter the biosignal using the HPF by the cut-off frequency for the high pass filtering of $1/(2\pi*R_f*C_f)$. Specifically, the biosignal may be filtered to the desired cut-off frequency using the HPF by controlling the resistance ($R_f$) of the first feedback resistor 131 and the resistance ($R_f$) of the second feedback resistor 132.

In the exemplary embodiment, a voltage ($V_o$) outputted via the output terminal 143 of the op-amp 140 may be calculated as $$V_o = V_{mid} + \frac{j\omega \cdot R_{f1} \cdot C_1}{1 + j\omega \cdot R_{f1} \cdot C_{f1}}(V_2 - V_1),$$

When the capacitance (C) of the first capacitor 111 and the capacitance (C) of the second capacitor 112 are identical, and the capacitance ($C_f$) of the first feedback capacitor 121 and the capacitance ($C_f$) of the second feedback capacitor 122 are identical, and the resistance ($R_f$) of the first feedback resistor 131 and the resistance ($R_f$) of the second feedback resistor 132 are identical, and the first voltage is $V_1$ and the second voltage is $V_2$.

The outputted voltage signal is transmitted to a predetermined signal processing module, and the signal processing module may process the voltage signal in various methods, and provide the user with the biosignal of the user, or analyze the biosignal.

Similar to the description above, a biosignal amplifying module according to an aspect of embodiment can amplify and filter a biosignal with a configuration of one op-amp and an HPF with one stage, thereby enabling miniaturization and slimming of a biosignal measurement apparatus including the biosignal amplifying module.

According to an embodiment, there is provided a biosignal amplifying device which can include a biosignal amplifying circuit having only one op-amp and an HPF with only one stage, thereby enabling miniaturization and slimming when the biosignal amplifying circuit is realized in a printed circuit board (PCB), or an application specific integrated circuit (ASIC) using a commercialized integrated circuit (IC).

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A biosignal amplifying device comprising:
    an operational amplifier (op-amp) including a first input terminal and a second input terminal;
    a capacitor load including a first capacitor which is connected with the first input terminal of the op-amp, and in which a first voltage is inputted from a first electrode, and a second capacitor which is connected with the second input terminal of the op-amp, and in which a second voltage is inputted from a second electrode;
    a feedback capacitor load including a first feedback capacitor coupled to the first input terminal and an output terminal, and a second feedback capacitor connected with the second input terminal;
    a feedback resistor load including a first feedback resistor coupled to the first input terminal and the output terminal, and a second feedback resistor coupled to the second input terminal; and
    a direct current (DC) offset voltage ($V_{mid}$) is supplied to the second feedback capacitor and the second feedback resistor,
    wherein a capacitance of the first capacitor and second capacitor is controllable to perform low pass filtering of an inputted biosignal, and
    a resistance of the first feedback resistor and second feedback resistor is controllable to perform high pass filtering of the inputted biosignal.

2. The biosignal amplifying device of claim 1, wherein the first feedback capacitor and the first feedback resistor are connected in parallel, and are coupled to the first capacitor.

3. The biosignal amplifying device of claim 1, wherein the second feedback capacitor and the second feedback resistor are connected in parallel, and are coupled to the second capacitor.

4. The biosignal amplifying device of claim 1, wherein the first electrode and the second electrode measure an electrocardiogram (ECG) signal of a user.

5. The biosignal amplifying device of claim 1, wherein a gain of the op-amp is set according to rates of any one capacitance from among the capacitor load, and any one capacitance from among the feedback capacitor load.

6. The biosignal amplifying device of claim 5, wherein the gain corresponds to $C/C_f$ when a capacitance (C) of the first capacitor and a capacitance (C) of the second capacitor are substantially identical, and a capacitance ($C_f$) of the first feedback capacitor and a capacitance ($C_f$) of the second feedback capacitor are substantially identical, and a resistance ($R_f$) of the first feedback resistor and a resistance ($R_f$) of the second feedback resistor are substantially identical.

7. The biosignal amplifying device of claim 1, wherein a cut-off frequency of the op-amp is set according to any one resistance from among the feedback resistor load, and any one capacitance from among the feedback capacitor load.

8. The biosignal amplifying device of claim 7, wherein the cut-off frequency corresponds to $1/(2\pi * R_f * C_f)$ when a capacitance (C) of the first capacitor and a capacitance (C) of the second capacitor are substantially identical, and a capacitance ($C_f$) of the first feedback capacitor and a capacitance ($C_f$) of the second feedback capacitor are substantially identical, and a resistance ($R_f$) of the first feedback resistor and a resistance ($R_f$) of the second feedback resistor are substantially identical.

9. The biosignal amplifying device of claim 1, wherein an output terminal voltage ($V_o$) of the op-amp is $$V_o = V_{mid} + \frac{j\omega \cdot R_{f1} \cdot C_1}{1 + j\omega \cdot R_{f1} \cdot C_{f1}}(V_2 - V_1),$$

when a capacitance ($C_1$) of the first capacitor and a capacitance ($C_2$) of the second capacitor are substantially identical, and a capacitance ($C_{f1}$) of the first feedback capacitor and a capacitance ($C_{f2}$) of the second feedback capacitor are substantially identical, and a resistance ($R_{f1}$) of the first feedback resistor and a resistance ($R_{f2}$) of the second feedback resistor are substantially identical, and the first voltage is $V_1$ and the second voltage is $V_2$.

10. The biosignal amplifying device of claim 1, wherein the first electrode and the second electrode are dry-type electrodes.

11. The biosignal amplifying device of claim 1, wherein the first electrode and the second electrode are wet-type electrodes.

12. The biosignal amplifying device of claim 1, wherein the device includes only one op-amp and a high pass filter with only one stage.

* * * * *